United States Patent
Bickelhaupt et al.

(10) Patent No.: US 11,899,089 B2
(45) Date of Patent: Feb. 13, 2024

(54) PHANTOM CALIBRATION BODY AND METHOD FOR DETERMINING AT LEAST ONE QUANTITATIVE DIFFUSION PARAMETER EXTRACTED FOR CHARACTERIZATION OF A TISSUE IN MAGNETIC RESONANCE IMAGING

(71) Applicant: Deutsches Krebsforschungszentrum, Heidelberg (DE)

(72) Inventors: Sebastian Bickelhaupt, Heidelberg (DE); Tristan Anselm Kuder, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 749 days.

(21) Appl. No.: 15/733,413

(22) PCT Filed: Jan. 24, 2019

(86) PCT No.: PCT/EP2019/051678
§ 371 (c)(1),
(2) Date: Jul. 23, 2020

(87) PCT Pub. No.: WO2019/145382
PCT Pub. Date: Aug. 1, 2019

(65) Prior Publication Data
US 2020/0348384 A1    Nov. 5, 2020

(30) Foreign Application Priority Data

Jan. 26, 2018 (EP) .................................... 18153618

(51) Int. Cl.
*G01R 33/58* (2006.01)
*A61B 5/055* (2006.01)
(Continued)

(52) U.S. Cl.
CPC ........... *G01R 33/58* (2013.01); *A61B 5/0042* (2013.01); *A61B 5/055* (2013.01); *A61B 5/4064* (2013.01);
(Continued)

(58) Field of Classification Search
CPC ............... G01R 33/58; G01R 33/4804; G01R 33/56341; A61B 5/0042; A61B 5/055; A61B 5/4064; G09B 23/286
See application file for complete search history.

(56) References Cited

U.S. PATENT DOCUMENTS

| 4,613,819 A * | 9/1986 | Chui ...................... G01R 33/58 324/318 |
| 2013/0200900 A1* | 8/2013 | Buurman ............... G01R 33/50 324/318 |

(Continued)

FOREIGN PATENT DOCUMENTS

| DE | 737 663 C | 7/1943 |
| DE | 10 2016 121 212 A1 | 6/2017 |

OTHER PUBLICATIONS

Keenan, K., et al. Design of a Breast Phantom for Quantitative Magnetic Resonance Imaging, Journal of Magnetic Resonance Imaging. vol. 44(3), 2016. p. 610-619 (Year: 2016).*
(Continued)

*Primary Examiner* — Keith M Raymond
*Assistant Examiner* — Sean A Frith
(74) *Attorney, Agent, or Firm* — Woodard, Emhardt, Henry, Reeves & Wagner, LLP (57) ABSTRACT

A phantom calibration body (110) for a method for determining at least one quantitative diffusion parameter extracted for characterization of a tissue being suspicious to a tumorous modification in magnetic resonance imaging is
(Continued)

disclosed, wherein the phantom calibration body (110) is designed for being characterized during characterization of the tissue by the magnetic resonance imaging. Herein, the phantom calibration body (110) comprises a first compartment (112) having a first cross-section, the first compartment (112) being filled with a first solution comprising a calibration substance having a first concentration; and a second compartment (114) having a second cross-section, the second cross-section having at least two different partitions with differing diameters, wherein the second compartment (114) is filled with a second solution comprising the calibration substance having a second concentration, the second concentration differing from the first concentration. The present invention allows determining absolute quantitative parameters in an individualized fashion for each individual tissue independent from various times of recording, applied software algorithms for post-processing of the raw MRI data, MR devices, or MR vendors. The present invention, thus, allows using the absolute quantitative data extracted from the phantom calibration body (110) measured with every tissue for comparability of quantitative data, being a prerequisite for introducing quantitative diffusion weighted imaging (DWI) into clinical routine.

16 Claims, 4 Drawing Sheets

(51) Int. Cl.
    *G01R 33/48*         (2006.01)
    *G01R 33/563*       (2006.01)
    *G09B 23/28*        (2006.01)
    *A61B 5/00*         (2006.01)

(52) U.S. Cl.
    CPC ... *G01R 33/4804* (2013.01); *G01R 33/56341* (2013.01); *G09B 23/286* (2013.01)

(56) References Cited

U.S. PATENT DOCUMENTS

| | | | | |
|---|---|---|---|---|
| 2015/0323639 | A1 | 11/2015 | Boss | |
| 2016/0038116 | A1* | 2/2016 | Sell | A61B 6/582 378/207 |
| 2016/0327625 | A1* | 11/2016 | Vermiglio | A61B 6/583 |
| 2016/0363644 | A1* | 12/2016 | Wang | G01R 33/58 |
| 2017/0192076 | A1* | 7/2017 | Kerins | G01R 33/58 |
| 2017/0242090 | A1 | 8/2017 | Horkay et al. | |

OTHER PUBLICATIONS

Partridge, S., et al. "Apparent Diffusion Coefficient Values for Discriminating Benign and Malignant Breast MRI Lesions: Effects of Lesion Type and Size," Women's Imaging Journal. vol. 194, 2010. p. 1664-1673 (Year: 2010).*

Freitag, M. T., et al. "Ausgewahlte klinisch etablierte und wissenschaftliche techniken der diffusionsgewichteten MRT," Der Radiologe, (Jan. 22, 2016), pp. 137-147. DOI 10.1007/s00117-015-0066-6.

Radbruch, A. et al. "Gadolinium retention in the dentate nucleus and globus pallidus is dependent on the class of contrast agent," Radiology, vol. 275, No. 3, (Jun. 2015), pp. 783-791. DOI 10.1148/radiol.2015150337.

Errante, Y., et al. "Progressive increase of T1 signal intensity of the dentate nucleus on unenhanced magnetic resonance images is associated with cumulative doses of intravenously administered gadodiamide in patients with normal renal function, suggesting dechelation," Investigative Radiology, (Oct. 2014), vol. 49, No. 10, pp. 685-690. DOI 10.1097/RLI.0000000000000072.

Kanda, T., et al. "High signal intensity in the dentate nucleus and globus pallidus on unenhanced T1-weighted MR images: Relationship with increasing cumulative dose of a gadolnium-based contrast material," Radiology, vol. 270. No. 3, (Mar. 2014), pp. 834-841. DOI 10.1148/radiol.13131669.

McDonald, R. J., et al. "Intracranial gadolinium deposition after contrast-enhanced MR imaging," Radiology. vol. 275, No. 3, (Jun. 2015), pp. 772-782. DOI 10.1148/radiol.15150025.

Othman, E., et al. "Comparison of false positive rates for screening breast magnetic resonance imaging (MRI) in high risk women performed on stacked versus alternating schedules," Springer Plus, vol. 4, No. 77 (Feb. 13, 2015). DOI 10.1186/s40064-015-0793-1.

Baltzer, P. A. T., et al. "False-positive findings at contrast-enhanced breast MRI: A BI-RADS descriptor study," American Journal of Roentgenology, vol. 194, No. 6, (Jun. 2010), pp. 1658-1663. DOI 10.2214/AJR.09.3486.

Quon, J. S., et al. "False positive and false negative diagnoses of prostate cancer at multi-parametric prostate MRI in active surveillance," SpringerLink, vol. 6, (May 23, 2015), pp. 449-463. DOI 10.1007/s13244-015-0411-3.

Bammer, R. "Basic principles of diffusion-weighted imaging," European Journal of Radiology, vol. 45, No. 3, (Feb. 28, 2003), pp. 169-184. DOI 10.1016/s0720-048x(02)00303-0.

Koh, D. M., et al. "Intravoxel incoherent motion in body diffusion-weighted MRI: Reality and challenges," American Journal of Roentgenology, vol. 196, No. 6, (Jun. 2011), pp. 1351-1361. DOI 10.2214/AJR.10.5515.

Yablonskiy, D. A., et al. "Statistical model for diffusion attenuated MR signal," Magnetic Resonance in Medicine, vol. 50, No. 4, (Oct. 2003), pp. 664-669. DOI 10.1.1.297.4800.

Jensen, J. H., et al. "Diffusional kurtosis imaging: The quantification of non-gaussian water diffusion by means of magnetic resonance imaging," Magnetic Resonance in Medicine, vol. 53, No. 6, (May 19, 2005), pp. 1432-1140 DOI 10.1002/mrm.20508.

Iima, M., et al. "Quantitative non-gaussian diffusion and intravoxel incoherent motion magnetic resonance imaging," Investigative Radiology, vol. 50, No. 4, (Apr. 2015), pp. 205-211. DOI 10.1097/RLI.0000000000000094.

Sui, Y., et al. "Differentiation of low- and high-grade gliomas using high b-value imaging with non-gaussian diffusion model," American Journal of Neuroradiology, vol. 37, No. 9, (Sep. 1, 2016), pp. 1643-1649. DOI 10.3174/ajnr.A4836.

Panagiotaki, E., et al. "Noninvasive quantification of solid tumor microstructure using VERDICT MRI," American Association for Cancer Research, vol. 74, No. 7, (Apr. 1, 2014), pp. 1902-1912. DOI 10.1158/0008-5472.CAN-13-2511.

Babieri, F., et al. "Differentiation of prostate cancer lesions with high and with low Gleason score by diffusion-weighted MRI," European Radiology, vol. 27, No. 4, (Apr. 13, 2016), pp. 1547-1555 DOI 10.1007/s00330-016-4449-5.

Wagner, F., et al. "Temperature and concentration calibration of aqueous polyvinylpyrrolidone (PVP) solutions for isotropic diffusion MRI phantoms," PLOS One, vol. 12, No. 6, (Jun. 19, 2017). DOI 10.1371/journal.pone.0179276.

Keenan, K. E., et al. "Quantitative magnetic resonance imaging phantoms: A review and the need for a system phantom," Magnetic Resonance in Medicine, vol. 79, No. 1, (Oct. 30, 2017), pp. 48-61. DOI 10.1002/mrm.26982.

Laun, F. B., et al. "Einfuhrung in die grundlagen und techniken der diffusionsbildgeung," Der Radiologe, vol. 51, No. 3, (Mar. 18, 2011), pp. 170-179. DOI 10.1007/s00117-010-2057-y.

Buzzelli, M., et al. "Initial performance of the diffusive quantitative imaging phantom (DQIP): Thermal and SNR characteristics using a clinical protocol," Proceedings of the International Society for Magnetic Resonance Medicine, (Apr. 2014).

Lavdas, I., et al. "A phantom for diffusion-weighted MRI (DW-MRI)," Journal of Magnetic Resonance Imaging, vol. 38, No. 1, (Apr. 10, 2013). DOI 10.1002/jmri.23950.

(56) References Cited

OTHER PUBLICATIONS

Kathryn E. Keenan et al: "Design of a breast phantom for quantitative MRI", J. Magn. Res. Imaging, vol. 44, No. 3, 2016, 610-619.

* cited by examiner

PHANTOM CALIBRATION BODY AND METHOD FOR DETERMINING AT LEAST ONE QUANTITATIVE DIFFUSION PARAMETER EXTRACTED FOR CHARACTERIZATION OF A TISSUE IN MAGNETIC RESONANCE IMAGING

TECHNICAL FIELD OF THE INVENTION

The invention relates to a phantom calibration body and a computer-implemented method for determining at least one quantitative diffusion parameter extracted for characterization of a tissue being suspicious to a tumorous modification in magnetic resonance imaging (MRI), wherein the phantom calibration body is used, as well as to a computer program product comprising executable instructions for performing the method. The phantom calibration body and the method according to the present invention may, specifically, be used in the field of oncologic imaging, wherein, however, other applications are feasible.

RELATED ART

Acquiring quantitative insights into microstructures of a tissue in the human body, in particular a tissue being suspicious to a tumorous modification, is still a challenging task, specifically, in the field of oncologic imaging. Oncologic imaging is, commonly, performed by using one or more imaging modalities which are currently available for detecting and characterizing suspicious changes of a tissue and that include ultrasound, x-ray imaging, computer tomography, positron emission tomography (PET), and magnetic resonance imaging (MRI), whereby especially MRI is increasingly used in oncologic imaging [1].

Using MRI for detecting and characterizing suspicious change of a tissue, commonly, includes sophisticated examination protocols using various imaging contrasts to visually characterize changes of an underlying tissue as well as an intravenous application of a contrast agent which, in particular, comprises gadolinium that may, however, imply risks for allergic reactions, nephrogenic systemic fibrosis, or gadolinium deposition in the brain [2-5].

In order to avoid such consequences, a different approach applies MRI sequences configured for mapping water diffusion [9]. This approach is based on the assumption that water diffusion is closely related to tissue properties. By way of example, water has been considered not to move as freely in malignant tissue as in benign tissue as a result of a restricted possibility of diffusion between densely packed cell conglomerates in the malignant tissue. Using diffusion weighted imaging (DWI) in connection with a proper setting of the corresponding MRI sequences may, thus, be advantageous in characterizing tissue changes by means of non-invasive imaging.

In addition, an in-depth analysis of DWI images might be useful for further insights into tissue properties which are correlated with histopathology. By applying various fitting models, DWI has been reported to allow assessing microstructural tissue properties which closely correlate to isolated aspects of the tissue, including tissue cellularity, such as indicated by an apparent diffusion coefficient (ADC), or tissue complexity, such as indicated by Kurtosis [10-14].

A similar approach is provided by a mathematical model which characterizes water diffusion in vascular, extra-cellular extra-vascular space (EES), and intracellular compartments in tumors [15]. For this purpose, a sum of three parametric models is calculated, wherein each parametric model describes a diffusion-related magnetic resonance signal in a separate population of water from one of the three components, wherein a first signal arises from intracellular water trapped inside cells while a second signal arises from EES water adjacent to, but outside cells and blood vessels and while a third signal arises from water in blood undergoing microcirculation in a capillary network. Since this model, however, does not incorporate an exchange between the three water populations, each quantification scheme is treated individually.

In a further approach [16], DWI of prostate and/or bladder cancer tissues scheduled for radical prostatectomy were acquired and used to compute the apparent diffusion coefficient (ADC), an intravoxel incoherent motion (IVIM: the pure diffusion coefficient $D_t$, the pseudo-diffusion fraction $F_p$ and the pseudo-diffusion coefficient $D_p$), and high b-value parameters within the index lesion. These parameters were, subsequently, used in a separate fashion or combined in a logistic regression model in order to differentiate lesions. In a similar manner, using a fractional order calculus model (FROC) in brain imaging was evaluated using an imaging protocol with more than 10 b-values to extract two parameters (D as an approximation of the apparent diffusion coefficient and $\beta$) which, separately or combined with a logistic regression model, was used for differentiating high grade from low grade brain lesions [17].

In order to be able to actually use the mathematical models and quantitative parameters characterizing water diffusion for clinical diagnostics, it is important to ensure that the quantitative parameters are obtained in a precise, accurate and repeatable fashion for each and every individual tissue in order to allow intra-individual comparison between different sequential examinations as well as inter-individual comparison between different origins of the tissue, MRI vendors, MRI devices, and evaluation software enabling the definition of quantitative cut-off values. Consequently, it would be highly desirable to have appropriate calibration measures which allow obtaining the quantitative parameters independently from the actual circumstances under which the corresponding measurements are performed.

However, it is generally known that the quantitative parameters which are extracted from diffusion MRI data may vary depending on temperature, between MRI devices with different field strengths, hardware construction details and/or versions, and between MRI vendors. Hereby, even extracted data from an identical MRI device can vary over time, wherein such variations may potentially be related to changes and/or modifications in the hardware system of a MRI device. Further, it is also generally known that applying different software for acquisition and/or post-processing of raw data can have an influence on the resulting data. Hereby, using periodic calibration of the MRI device itself may, however, not sufficiently ensure that identical quantitative parameters are obtained for individual MRI measurements.

In order to overcome this situation, it has been proposed in a further approach to use a phantom calibration body for calibrating an MRI device in a periodical manner, e.g., in US 2017/0242090 A1, US 2015/0323639 A1, or DE 10 2016 121 212 A1, wherein the phantom calibration bodies as disclosed therein are used for calibrating the MRI device. Further, [18] describes a phantom compartment which is filled with a known solution being capable for determining quantitative DWI parameters when analyzing the ADC, wherein it is supposed that the temperature of the solution is known, which is ensured by applying a thermometer provided in a storage case. However, since this kind of calibration is not related to a particular tissue, a clinical applicability of this approach is significantly limited. In particular, if a later measurement is performed at the same tissue using a different or even the identical MRI device, the later acquired data are, still, not comparable with previously acquired data since the calibration results obtained from the periodic measurements have not been related to each tissue data set.

Further, [19] describes a breast phantom designed to enable quantitative assessment of measurements of $T_1$ relaxation time, apparent diffusion coefficient (ADC), and other attributes of breast tissue. Herein, a breast phantom was created with two independent, interchangeable units for diffusion and $T_1/T_2$ relaxation, each with flexible outer shells. The $T_1$ unit was filled with corn syrup solution and grapeseed oil to mimic the relaxation behavior of fibroglandular and fatty tissues, respectively. The diffusion unit contains plastic tubes filled with aqueous solutions of polyvinylpyrrolidone (PVP) to modulate the ADC. The phantom was imaged at 1.5 T and 3.0 T using MRI scanners and common breast coils from multiple manufacturers to assess $T_1$ and $T_2$ relaxation time and ADC values.

Further, DE 10 2016 121212 A1 discloses an MRI phantom for determining the measurement quality of an MRI system, comprising a three-dimensional fluid-filled body for introduction into a measurement area of the MRI system, wherein at least one dissolution sample is positioned in the body, which comprises a plurality of well-defined structures of different size and/or different ADC values, which allow a determination of the measurement quality of the MRI system at the position of the dissolution sample in the body of the phantom. Further, a dissolution sample for use in an MRI phantom and a method for temperature measurement in an MRI phantom, in particular in a dissolution sample of an MRI phantom, is disclosed.

Problem to be Solved

It is therefore an objective of the present invention to provide a phantom calibration body and a computer-implemented method for determining at least one quantitative diffusion parameter extracted for characterization of a tissue being suspicious to a tumorous modification in magnetic resonance imaging (MRI) as well as a computer program product comprising executable instructions for performing the method, which at least partially avoid the disadvantages of known methods and devices.

In order to achieve an adequate level of precision and accuracy for using quantitative diffusion MRI data for clinical routine, it would, thus, be desirable that the obtained diffusion MRI data could undergo further steps which are related to calibration, standardization, and/or quality control of the data with respect to each individual tissue when using quantitative measures of DWI-derived parameters in order avoid that the extracted quantitative parameters may depend on various factors, including but not limited to tissue temperature, MRI device, or MRI vendor.

SUMMARY OF THE INVENTION

This problem is solved by a phantom calibration body and a computer-implemented method for determining at least one quantitative diffusion parameter extracted for characterization of a tissue being suspicious to a tumorous modification in magnetic resonance imaging (MRI) as well as a computer program product comprising executable instructions for performing the method according to the independent claims. Further, preferred embodiments of the invention, which may be realized in an isolated way or in any arbitrary combination, are disclosed in the dependent claims.

As used in the present specification, the term "comprising" or grammatical variations thereof, are to be taken to specify the presence of stated features, integers, steps or components or groups thereof, but do not preclude the presence or addition of one or more other features, integers, steps, components or groups thereof. The same applies to the term "having" or grammatical variations thereof, which is used as a synonym for the term "comprising".

As further used herein, the expressions "have", "comprise" and "contain" as well as grammatical variations thereof are used in a non-exclusive way. Thus, the expression "A has B" as well as the expression "A comprises B" or "A contains B" may both refer to the fact that, besides B, A contains one or more further components and/or constituents, and to the case in which, besides B, no other components, constituents or elements are present in A.

In a first aspect of the present invention, a phantom calibration body is disclosed. As generally used, the term "phantom calibration body", herein also abbreviated to the term "phantom", refers to an artificial object, which is, specifically, designated for mimicking a particular value of a diffusion coefficient, wherein the value of the diffusion coefficient may, especially, be in a relationship to a selected tissue, wherein the phantom is designed for being characterized during characterization of the tissue by at least one imaging device, specifically by an magnetic resonance imaging (MRI) device as described below in more detail.

According to the present invention, the phantom calibration body comprises:
 a first compartment having a first cross-section, the first compartment being filled with a first solution comprising a calibration substance having a first concentration; and
 a second compartment having a second cross-section, the second cross-section having at least two different partitions with differing diameters, wherein the second compartment is filled with a second solution comprising the calibration substance having a second concentration, the second concentration differing from the first concentration.

Accordingly the phantom calibration body comprises at least two individual compartments which at least partially, preferably completely, filled with two individual solutions that have different concentrations of the calibration substance, wherein the two compartments are distinguished with respect to each other by having different cross-sections. As generally used, the term "compartment" refers to an individual partition of the body which is separated from many other compartment by having at least four sides, preferably five sides or six sides which, specifically, are designed in a manner that an unintentional exchange of liquids, in particular of the solutions, between different compartments is excluded. Herein, form, size, and respective arrangement of the two individual compartments are provided in a manner that the two individual compartments of the phantom calibration body are adapted for mimicking two types of the tissues, specifically, the benign tissue and the malignant tissue, of an examined body region. In addition, one or more further compartments may be comprised by the phantom calibration body, wherein a further compartment may have a further cross-section and may be filled with a further solution which may comprise the calibration substance having a further concentration, wherein the further concentration may, preferably, differ from the first concentration and/or the second concentration.

As generally used, the term "tissue" refers to a partition of an animal body, preferably of a mammal body, and, more preferred of a human body, which comprises an ensemble of similar cells having a similar origin and which are assembled together to jointly performing a particular function in the body. Consequently, the tissue can be considered as a cellular organization which is arranged at an intermediate level between a single cell and a complete organ, wherein the organ can be considered as being formed by functionally arranging a plurality of tissues. By way of example, in a phantom which may specifically be designed for an examination of mammal liver, the first compartment of the phantom is filled with a first concentration of the calibration substance which is adapted for mimicking healthy liver tissue as known from literature while the second compartment is filled with a second concentration of the calibration substance which is adapted for mimicking malignant liver lesions as, again, known from the literature. As described below in more detail, a graphical representation of the raw signal intensity or, alternatively or in addition, of at least one quantitative diffusion parameter of the tissue, specifically an ADC map, of the phantom can be determined from acquired MRI data, wherein the different compartments are expected to provide different results due to the different concentrations. Herein, the term "ADC" refers to an 'apparent diffusion coefficient' as explained below in more detail.

As indicated above, the two compartments are distinguished with respect to each other by having different cross-sections. As further indicated above, the second cross-section of the second compartment comprises two or more different partitions having differing diameters with respect to each other. As generally used, the term "cross-section" refers to a form of a traverse section of the selected compartment, wherein the term "diameter" relates to a distance from one side of the body to an opposing side of the body, both sides cut by the selected cross-section. Herein, the second cross-section may, preferably, exhibit a continuous variation of the diameter along an extension of the second compartment whereas, in contrast hereto, a variation of the first cross-section along an extension of the first compartment may be lower, preferably considerably lower, specifically negligent. In a particularly preferred embodiment, the second cross-section may, thus, have a pair of opposing sides along an expansion of the second receptacle herein the opposing sides may, preferably, exhibit a non-parallel arrangement in a manner that the pair of the opposing sides may be inclined by an angle of 5° to 45°, specifically of 15° to 30°, with respect to each other. As a result, the second compartment may, thus, specifically comprise a triangularly varying cross-section along the expansion of the second compartment. In this embodiment, an evaluation of the ADC map of the phantom may particularly be straightforward. However, other forms being selected for the second compartment may be also feasible as long as the second cross-section of the second compartment comprises two or more different partitions having differing diameters which can be used for a purpose of comparison of the second cross-section to the first cross-section within the ADC map. As described below in more detail, a minimum size of a lesion which can still be reliably differentiated between the two types of the tissues, specifically, between the benign tissue and the malignant tissue, of the examined body region, can, thus, be determined from the ADC map. Returning to the above-mentioned example of the phantom specifically designed for the examination of mammal liver, may allow determining that in an individual tissue malignant liver lesions of a size of 4 mm can still reliably be differentiated from healthy tissue by using a DWI sequence. Further examples are possible.

In a preferred embodiment of the phantom calibration body, in particular in the phantom as used in the example below, the first compartment can comprise a first receptacle while the second compartment can comprise a second receptacle, wherein both the first receptacle and the second receptacle may be comprised by a container, preferably by a single container which may be adapted in form, size, and orientation to receive both the first receptacle and the second receptacle, in particular in a manner that the container may entirely be filled by the both the first receptacle and the second receptacle. In this embodiment of the phantom calibration body, in particular in the phantom used in the example below, the container may be provided as the first receptacle whereas the second receptacle can be comprised by the first receptacle, in particular, by inserting the second receptacle into the container which constitutes the first receptacle. However, further kinds of arrangements may also be feasible as long as the second cross-section of the second receptacle comprises two or more different partitions having differing diameters.

As already indicated above, the two individual compartments of the phantom are at least partially, preferably completely, filled with two individual solutions which have different concentrations of the same calibration substance. As generally used, the term "filled" refers to a situation in which a volume of the respective compartment which is adapted to receive the particular solution, at least predominantly, preferably to at least 75%, more preferred to at least 90%, comprises the particular solution. Herein, in a particular embodiment one or both of the two individual compartments which are filled with the same calibration substance are closed thereafter without being able to be reopened without a danger of destroying the respective compartment, such as by applying an adhesive or a welding procedure to the respective opening. However, in an alternative embodiment, in the phantom calibration body, in particular in the phantom as used in the example below, each of the compartments comprises at least one individual opening which is designed for filling the corresponding solution into the respective compartment. As a result of the individual openings for each of the compartments, each compartment may actually receive the desired concentration of the individual solution having the predefined concentration of the same calibration substance. However, further kinds of arrangements intended for filling both compartments of the phantom in the desired manner may also be feasible.

In a particularly preferred embodiment, the phantom calibration body is at least partially, preferably completely, filled with the calibration substance which may, in particular be selected from one of polyvinylpyrrolidone (PVP), a polyvinyl alcohol, a polyacrylamide, a polyacrylate, a polyethylene glycol, a polysaccharide, cellulose, a derivative thereof, or a copolymer thereof. However, further substances which are known for this purpose may also be feasible as long as they are capable of proving a first concentration and a second concentration which may be adapted for mimicking the two different types of the tissue as indicated elsewhere in this document in more detail. In addition, the phantom may comprise signal bearing substances selected from paramagnetic solutions, pure gels of gelatin, agar, polyvinyl alcohol, water soluble silicone compounds, polyacrylamide, agarose, organic doped gels, gels doped with at least one paramagnetic additive or an animal derived substance including but not limited to diary cream, yogurt, bacon or a reverse micelle solution, and an oily or a fatty substance. Still, further substances may also be applicable.

In particular, the solution of the calibration substance may, preferably, be an aqueous solution of the calibration substance, wherein the first concentration and the second concentration may, preferably, be selected from a concentration of 0.01% to 100%, wherein all percentages % are provided herein in % (w/w). Herein, the second concentration may, preferably, differ from the first concentration by at least 0.1%, more preferred by at least 1%, specifically by at least 5%. Herein, the first concentration may, preferably, be selected of 5% to 60%, more preferred of 10% to 40%, specifically of 15% to 25%, whereas the second concentration may, preferably, be selected of 20% to 75%, more preferred of 25% to 50%, specifically of 30% to 40%. The ranges as provided herein are, in particular, applicable to PVP which is, specifically, used as the calibration substance in the phantom of the particularly preferred example below.

In a particularly preferred embodiment, the first solution and the second solution have a single K-value, such K15, K30 or K90 in the case of PVP. As generally used, the terms "K-value" or "Fikentscher K-value" refer to a molecular weight of polymers such as polyvinylchloride (PVC) or polyvinylpyrrolidone (PVP), wherein a relationship between an intrinsic viscosity, the K-value, and an approximate molecular weight is known to the skilled person may be retrieved from tables comprised in the literature. Thus, in further contrast to the known state of the art, such as expressed in US 2017/0242090 A1, the calibration substance does not comprise a dedicated mixture of polymers having a high molecular weight and a low molecular weight but only a regular solution having a molecular weight which is, generally, referred to as a single K-value in a purity and predominance of single molecular weights as typically achieved in the standard products.

In a preferred embodiment, each of the compartments may be or comprise a solid plastic structure in form of a receptacle which may be filled with the desired solution. Herein, the second compartment may be formed, as shown below in the examples, as a triangular inlay, wherein the inlay may also be rotatable around one or more axes of the receptacle. As a result, such an interleaved interlaced design of the two compartments as comprised by the phantom allows, as described below in more detail, analyzing a differentiability of the MRI between different concentrations of the calibration substance, thus, mimicking an ability to differentiate between different tissue structures, e.g. benign tissue and malignant tissue, and assessing a minimum resolution of the MRI, specifically determining a resolution with regard to depicting small details of the tissue under examination.

In a further preferred embodiment, the phantom may be stored inside the scanner room in a plastic box together with a thermometer, specifically a calibrated thermometer. As an alternative, the thermometer, specifically a short-length thermometer, such as an alcohol thermometer or a thermocouple, may also be embedded at least partially, preferably completely, within the phantom, especially within the container being or comprising the first compartment. However further locations for placing the thermometer may also be suitable. Irrespective of the location, the thermometer may be used herein in order to determine and, if applicable, to correct any effect based on a variation of the temperature as determined by the thermometer.

Advantageously, the design of the phantom calibration body according to the present invention allows placing the phantom in a vicinity of the tissue, such as at a side of the tissue, during MR examination in a manner of easy placement and removal. Herein, the design of the phantom can be selected with respect to an individual design of the MR coils of different MR vendors or MR coil vendors so that, in general, the phantom can be placed within one of the MR coils of the MRI device. For example, the phantom may be placed in an opening of the body matrix coil. Thus, the phantom may, in general, be placed in each MR vendor machine independent of the actual coil design. Before placing the phantom in the vicinity of the tissue, the thermometer as being present in a phantom storage case may be used to assess the phantom temperature, which may, subsequently, be noted, for example, by using an MR scanner software in the MR sequence description. The phantom may, thus, preferably be placed in the vicinity of the tissue immediately before starting an MR measurement in order to avoid a significant temperature change due to body heat.

In a further aspect of the present invention, a computer-implemented method for determining at least one quantitative diffusion parameter extracted for characterization of a tissue being suspicious to a tumorous modification in magnetic resonance imaging (MRI) is disclosed, wherein the tissue may, preferably, be provided by an animal, more preferably by a mammal, and, most preferably by a human. Herein, the method according to the present invention comprises at least the following steps a) to step c), wherein, however, additional steps may further be performed. In one embodiment, steps a) to c) may be performed in a sequential approach, commencing with step a), continuing with step b), and finishing with step d), wherein, however, a subsequent step may at least partially be performed concurrently with a previous step. In an alternative embodiment, the mentioned steps may be performed in an integrative approach or in a mixed approach combining the sequential approach and the integrative approach, in particular, for minimizing time and/or storing space required for performing the present method.

In particular, the method according to the present invention comprises the steps of:
a) placing a phantom calibration body as described elsewhere in this document in a vicinity of the tissue;
b) receiving raw magnetic resonance imaging (MRI) data being recorded by applying at least one diffusion weighted imaging (DWI) sequence concurrently to the tissue and to the phantom calibration body;
c) extracting at least one quantitative diffusion parameter of the tissue from the raw MRI data, wherein the corresponding quantitative diffusion parameter of the phantom calibration body is considered.

Thus, the present method, in general, refers to a characterization of a tissue by applying magnetic resonance imaging (MRI) as a non-invasive imaging modality. Herein, an invasive study of the tissue is known as "histology" or, in connection with a disease, as "histopathology". As described below in more detail, histopathological analyses have been used in order to demonstrate that the results being obtained for the tissues by the non-invasive characterization method according to the present invention actual confirm the findings in the suspicious tissues. In contrast hereto, the term "non-invasive" refers to an in vivo method of studying one or more tissues, wherein the tissue under investigation is able to remain in the body during the study. Thus, in contrast to a histopathological analysis, the non-invasive method of magnetic resonance imaging (MRI) as used herein allows determining one or more properties of the tissue without removing it from the body of a person or an animal.

Further, the preferred non-invasive method for characterizing tissue changes comprises diffusion weighted imaging (DWI) in connection with a proper setting of MRI sequences which are, especially, configured for mapping water diffusion. This approach reflects that water diffusion can reasonably be assumed to be related to tissue properties which appear relevant with regard to a tumorous modification of the tissue. As generally used, the term "tumorous modification" refers to a change of a particular tissue which can be attributed to a presence of a tumor in the particular tissue. Since the presence of a tumor tends to reorganize the cells in the particular tissue, such as, directed to generating more densely packed cell conglomerates, a movement of water molecules may be slightly impaired by the presence of a tumor in the particular tissue. Thus, diffusion may slightly be impaired between the cell conglomerates, resulting in a decrease of diffusion-related properties of the particular tissue. The tumorous modification can, in general, be assigned to a presence of cancer within the tissue. The term "cancer" in the context of this invention refers to a disease of an animal, in particular of a mammal, and, especially of a human, which is characterized by an uncontrolled growth by a group of body cells, usually denoted as "cancer cells". Further, the tumorous modification can be sorted into one of two classes "benign" or "malignant", wherein the term "malignant" relates to a particular tissue modification which is not self-limited in growth, capable of invading into adjacent tissues, and capable of spreading to distant tissues while the term "benign" refers to a particular tissue modification which does not comprise any of the mentioned properties of the malignant stage. However, classifying the tumorous modification of the tissue in an alternative manner may also be feasible.

Further, the method according to the present invention is a computer-implemented method. As generally used, the term "computer-implemented method" refers to a method which involves a programmable apparatus, in particular, a computer, a computer network, or a readable medium carrying a program, whereby one or more of the features of the invention are performed by means of at least one program. With particular regard to the present invention, the present method is, thus, being performed on a programmable apparatus which is configured for this purpose, such as by providing a particular computer program. As a result, the present method may, as demonstrated below in more detail, particularly affect the efficiency of determining one or more quantitative diffusion parameters extracted for the characterization of the tissue in MRI, thereby providing highly reliable results, thus, avoiding false positive findings which may result from invasive procedures to healthy persons as well as anxiety, stress and potential side-effects, such as bleeding, scars, or fistulas, due to a biopsy.

According to step a), a phantom calibration body is placed in a vicinity of the tissue. For further details with respect to the phantom calibration body reference may, thus, be made to the description of the phantom calibration body elsewhere in this document. As used herein, the term "in a vicinity" refers to a placement of the phantom such that a single image of the tissue under examination and of the phantom calibration body can be obtained. As described elsewhere in this document in more detail, the phantom calibration body can, in particular, have a design which may allow placing the phantom within one of the MR coils of the MRI device. Thus, the phantom may, in general, be placed in each MR vendor machine independent of the actual coil design.

According to step b), raw magnetic resonance imaging (MRI) data are received by applying at least one diffusion weighted imaging (DWI) sequence concurrently to the tissue and to the phantom calibration body. As generally used, the terms "magnetic resonance imaging" or "MRI" refer to a process which is, in particular, used for obtaining images ("MRI images") of an animal body, preferably of a mammal body, and, more preferred of a human body, or a partition thereof, such as a particular organ or tissue, in both health and disease, wherein the desired MRI images are generated by applying a magnetic resonance imaging device ("MRI device") which is configured for providing strong magnetic fields, magnetic field gradients and/or electromagnetic waves in the radiofrequency spectral range. For this purpose, the raw data may be acquired by using a known MRI device and a strength of the magnetic field of 1 T to 14 T, such as 1.5 T or 3 T.

With particular regard to the present invention, the raw data are acquired by applying at least one diffusion weighted imaging (DWI) sequence using at least two different b-values to the tissue under investigation. As mentioned above, the DWI sequences are MRI sequences which are, specifically, configured for mapping water diffusion in the tissue being investigated. As generally used, the term "MRI sequence" refers to a predefined succession of radiofrequency pulses and related magnetic field gradients, wherein the succession and the particular parameters with respect to each radiofrequency pulse and each related magnetic field gradient are configured in order to provide at least one particular MRI image which is, especially, configured for a particular purpose, wherein the particular purpose is related to diffusion weighting in the case of the present invention. By way of example, DWI sequences can be provided by using technical equipment associated to the MRI device, such as coils with a particular numbers of channels. The raw data can be acquired by employing a particular DWI sequence, such as EPI-DWI, Resolve-DWI, or DWIBS. Herein, a particular setting may be used for the selected DWI sequence which may be adjusted to a slice thickness, a fat saturation or to a different parameter. However, other kinds of DWI sequence may also be feasible. As further used herein, the term "raw data", thus, refers to primary data which are provided by the MRI device, such as a particular MRI image or at least one specific parameter which is related to the particular MRI image, whereby the parameters of the selected DWI sequence and the related particular setting are, additionally taken into account. Hereby, the raw data has, in general, not been subjected to processing by software designated for such a purpose.

As a result, the raw MRI data are received for the at least one DWI sequence for further processing in the subsequent step c). As generally used, the term "receiving data" refers to a process of obtaining data, specifically, the MRI raw data, by the MRI device, wherein the raw data may, preferably, be stored and prepared for the further processing. Further, additional pre-processing steps, such as removing outliers, may also be applied to the raw data prior to further processing in the subsequent step c).

According to step c), at least one quantitative diffusion parameter of the tissue is extracted from the raw MRI data, wherein the corresponding quantitative diffusion parameter of the phantom calibration body is considered. As further used herein, the term "extracting" refers to applying the at least one quantification scheme, wherein the quantification scheme is related to diffusion properties of the tissue, by using any process which is known in the art as being suitable for a quantification of DWI sequences, in particular but not limited to 'diffusional kurtosis imaging' (DKI), 'apparent diffusion coefficient' (ADC), Intravoxel incoherent motions'

(IVIM), or 'fractional order calculus' (FROC). Herein DKI, in general, takes into account a non-Gaussianity of a distribution. While the ADC approach assumes a mono-exponential decay of the diffusion signal, IVIM takes into account that flowing blood may contribute to the diffusion signal by employing a bi-exponential model, wherein a faster decaying exponential may be separable from a slower exponential decay reflecting true water diffusion. Further, the FROC analysis is adapted to determine a tissue heterogeneity in detected lesions within the tissue. In particular, a fitting procedure may, preferably, be applied for quantitatively determining the quantification scheme parameters from the applied quantification scheme. However, other methods may also be feasible.

A specific parameter which is used in recording and evaluating a particular DWI sequence is a so-called "b-value". Herein, the term "b-value" refers to a factor which is correlated with a magnetic field gradient being used for generating at least one DWI, whereby a higher b-value, in general, correlates with stronger diffusion effects. As most commonly used, an 'apparent diffusion coefficient' (ADC) may be estimated as a particular quantitative diffusion parameter after applying a particular DWI sequence to the tissue by using Equation (1) as $$S(b) = S_0 \cdot e^{(-b \, ADC)} \quad (1)$$

Here, S(b) denotes the diffusion-weighted signal in an imaging volume element in human body tissue or measurement object for a specific strength b of the diffusion weighting, and $S_0$ is the signal without diffusion weighting. Thus, acquiring images with at least two different b-values entered in the user interface of the MR device allows estimating the apparent diffusion coefficient ADC. Since the term $e^{(-b \, ADC)}$ in Equation (1) is a dimensionless number, the unit for b is the inverse of the unit for D. As a result, b is expressed as value of time per area, wherein the b-value may, preferably, be selected from a value of 0 to 4000 s/mm². For further details, reference may be made to [20].

In particular, by applying Equation (1) to a volume of interest in the solutions as comprised by the phantom calibration body, and by using a known ADC value for the solution at a given temperature as well as a the signal $S_0$ acquired for b=0, the actually applied b-values by the MR scanner can be estimated, which may be different from the b-values being entered by an operator into the MR scanner user interface. These kind of corrected b-values may, subsequently, be used in order to determine the desired corrected parameter maps, specifically of a raw signal intensity map or the ADC map, acquired, simultaneously, for the tissue during the same measurement.

Alternatively or in addition, the diffusion-weighted signal may be described in a further quantification scheme based on 'diffusional kurtosis imaging' (DKI) according to Equation (2) as $$S = S_0 \cdot e^{\left(-bD_K + \frac{1}{6}b^2 D_K^2 K\right)}, \quad (2)$$

wherein $S_0$ is the baseline magnetic resonance signal, b the b-value, $D_K$ the diffusion coefficient, and K the diffusional kurtosis coefficient (DKC) as a further quantitative diffusion parameter which can be obtained by fitting Equation (2) to a measured signal. By using a further quantification scheme, a different relationship for the b-value may also be applicable. As a further alternative, more complex steps using different sophisticated algorithms might also be feasible for the purposes of the present invention.

Further, using a known observation, that, for effectively free diffusion as it may be the case in a compartment with a homogenous solution of the calibration substance, the diffusional kurtosis coefficient K in Equation (2), wherein the K value may, preferably, be close to zero [12], another verification of the image quality can be performed. When performing a fitting procedure by applying Equation (2), an additional noise correction, specifically the noise correction as described in [12], may, preferably, by applied to the signal in a volume of interest in the phantom comprising a single concentration of the calibration substance, wherein a K value significantly different from zero may, thus, indicate an incorrect application of at least one of the diffusion-weighting magnetic field gradients or a signal contamination that may be caused by imaging artifacts.

Thus, by using the selected quantification scheme, the quantitative diffusion parameter, in particular the apparent diffusion coefficient (ADC) or, alternatively, the diffusional kurtosis coefficient (DKC), of the tissue is extracted from the raw MRI data, wherein the resulting quantitative diffusion parameter for the tissue is, subsequently, modified by taking into account the corresponding quantitative diffusion parameter of the phantom calibration body. As used herein, the term "modifying" refers to applying a post-processing procedure to a particular value of the quantitative diffusion parameter of the tissue, such as by using an MRI post-processing software or a software installed at the MRI device by the MRI vendor, after the particular measured value has been recorded by the MRI device, preferably, stored in a data storage, and evaluated in order to provide the related quantitative diffusion parameter for the tissue. As further used herein, the terms "considering" or "taking into account" refer to using at least one measured value for the phantom calibration body when modifying the particular value of the quantitative diffusion parameter of the tissue by applying the selected post-processing procedure. In a particularly preferred embodiment, the following quantitative values may be obtained during step c), in particular an individual image resolution of the MRI image of the issue;

an individual quality of the MRI image of the issue;

a quantitative value assessed in one or both of the compartments of the phantom calibration body; and quantitative data configured for modifying the quantitative diffusion parameter of the tissue individual for each origin of the tissue, specifically a patient.

With respect to an individual image resolution of the MRI image of the issue, using the recorded data of the phantom, thus, allows assessing an actual geometric image resolution which has been acquired during the tissue examination. Hereby, it can, preferably, be taken into account that both the first concentration and the second concentration of the calibration substance within the two compartments of the phantom calibration body, respectively, are known. As a result, the at least one quantitative diffusion parameter, such as the ADC value within the two compartments of the phantom can, thus, be assigned to a particular concentration of the calibration substance. As a result, the corresponding data which are related to each single origin of the tissue, specifically to a patient, in particular, a minimum extent of alterations of the tissue that can be visualized, can be obtained. Such a kind of analysis can be performed by using a particular software, preferably, by an existing software being adapted for assessing image resolution in MRI.

Herein, an individual quality of the MRI image of the issue may, preferably, be estimated in terms of an ability to be capable of differentiate between two types of tissues, specifically, between benign tissue and malignant tissue. For this purpose, the phantom as described elsewhere herein has two different compartments comprising two individual solutions having different concentrations of the same calibration substance, whereby the two types of the tissues, specifically, the benign tissue and the malignant tissue, of the examined body region may be mimicked. From the acquired raw MRI data a graphical representation of the raw signal intensity at different b-values or, alternatively or in addition, of the at least one quantitative diffusion parameter of the tissue, preferably, a two-dimensional representation ("map") or a three-dimensional representation of a selected quantitative diffusion parameter of the tissue, specifically a raw signal intensity map or, alternatively or in addition, an ADC map of the phantom can be determined, wherein the two different receptacles are expected to provide different areas in the raw signal intensity map or in the ADC map, respectively, at different b-values to the different concentrations of the calibration substance within the two different receptacles. Since the second compartment, as described elsewhere in in this document in more detail, comprises a second cross-section having at least two different partitions with different diameters, specifically, a triangularly varying cross-section along an expansion of the second compartment, a minimum diameter can be determined at which differences to the first cross-section can, still, be distinguished from the raw signal intensity map or the ADC map, respectively, at different b-values. Using this minimum diameter for which differences are, still, distinguishable in the raw signal intensity map or in the ADC map, respectively, at different b-values, a minimum size of a lesion which can still be reliably differentiated between the two types of the tissues, specifically between the benign tissue and the malignant tissue, of the examined body region, can be determined. As a result, this feature may, thus, allows assessing a minimum extent of tissue alterations which can be visualized in each single tissue, wherein this analysis can be performed by using new or existing software to assess image resolution in MR imaging. By way of example, the phantom as used herein may allow determining that, by using a particular DWI sequence in an individual tissue, malignant liver lesions of a size of 4 mm can still be reliably differentiated from healthy liver tissue. This value may be obtained from the corresponding cross-section of the second compartment, wherein a differentiation between the two compartments is still possible in the raw signal intensity map or in the ADC map, respectively, at different b-values thereof.

Thus, by assessing quantitative parameters of the phantom individually for each tissue, specifically each patient, may allow determining absolute quantitative parameters in an individualized fashion for each individual tissue, specifically each patient individual patient. Using these quantitative parameters extracted from the phantom, the data obtained from human tissue can now be modified when compared between various times of recording, applied software algorithms for post-processing of the raw MRI data, MR devices, MR vendors, etc. In contrast to the current state of the art, the present invention allows using the absolute quantitative data extracted from the phantom measured with every tissue, specifically each patient, for comparability of quantitative data, which appears as a prerequisite for introducing quantitative DWI imaging into clinical routine.

In a further aspect, the present invention refers to a computer program product which comprises executable instructions for performing a method according to the present invention. For this purpose, a computer program may comprise instructions provided by means of a computer program code which are capable of performing any or all of the steps of the methods according to the present invention and, thus, to establish a classification process when implemented on a computer or a data processing device. The computer program code may be provided on a data storage medium or a separate device such as an optical storage medium, e.g., a compact disc, or directly on a computer or data processing device.

SHORT DESCRIPTION OF THE FIGURES

Further optional details and features of the present invention may be derived from the subsequent description of preferred embodiments, preferably in combination with the dependent claims. Therein, the respective features may be realized in an isolated way or in arbitrary combinations. The invention is not restricted to the preferred embodiments. Identical reference numbers in the figures refer to identical elements or to elements having identical or similar functions or to elements corresponding to each other with regard to their functionality. Herein

DESCRIPTION OF PREFERRED EMBODIMENTS

Figure 1:
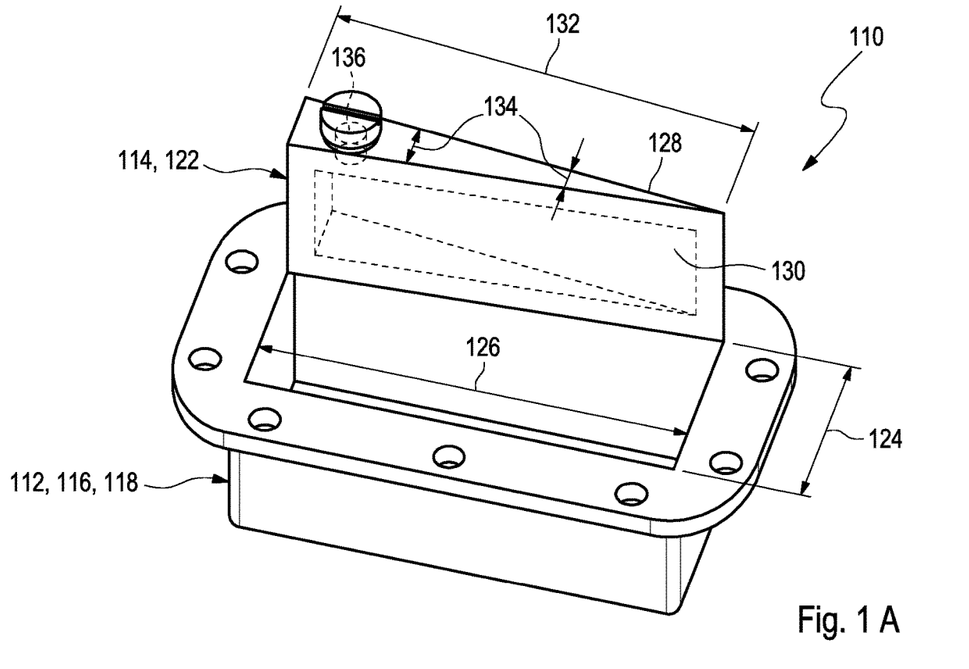
FIGS. 1A to 1F illustrate various views from different perspectives of a particularly preferred embodiment of a phantom calibration body according to the present invention.
Figure 2:
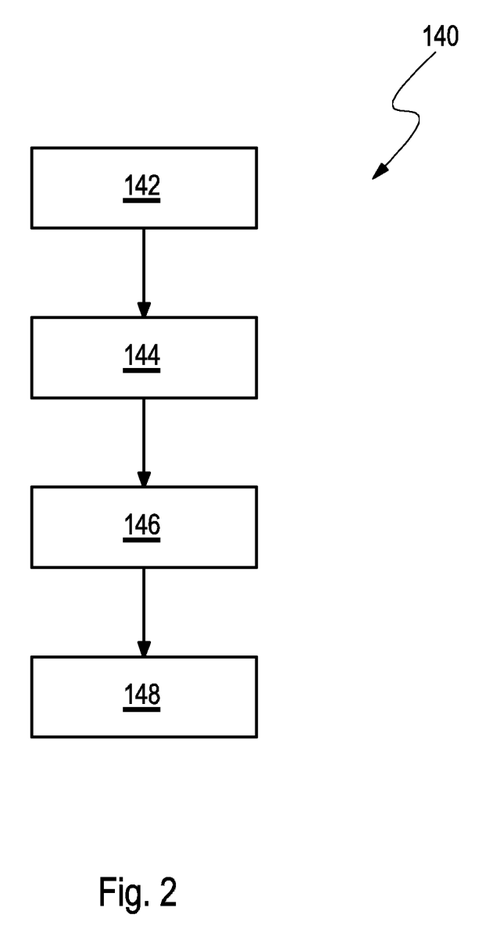
FIG. 2 schematically illustrates a computer-implemented method according to the present invention.

FIGS. 1A to 1F illustrate various views from different perspectives of a particularly preferred embodiment of a phantom calibration body 110 according to the present invention which is specifically adapted for being used in a computer-implemented method for determining at least one quantitative diffusion parameter extracted for characterization of a tissue being suspicious to a tumorous modification in magnetic resonance imaging (MRI), preferably as illustrated in FIG. 2. The phantom calibration body 110 and the corresponding method may, specifically, be used in the field of oncologic imaging, wherein, however, other applications are feasible.

The phantom calibration body 110 as shown in any one of FIGS. 1A to 1F comprises two individual compartments 112, 114, i.e. a first compartment 112 and a second compartment 114, wherein each of the compartments 112, 114 represent an individual partition of the calibration body 110 which is separated from the other compartment 112, 114. As a result of this particular arrangement, an unintentional exchange of liquids, in particular of the solutions as described above and/or below in more detail, from the first compartment 112 to the second compartment 114 or vice-versa is excluded.

As schematically depicted in FIGS. 1A and 1C to 1F, the first compartment 112 of this exemplary embodiment of the phantom calibration body 110 is implemented as a first receptacle 116 having a form of a container 118 comprising a first volume which is generated by five sides of the container 118 which can, as shown in FIGS. 1D to 1F, additionally be closed by a separate lid 120 which constitutes here a sixth side of the container 118.

In contrast hereto, the second compartment 114 of this exemplary embodiment of the phantom calibration body 110 is implemented as a second receptacle 122 comprising a second volume which is generated by five sides of the second receptacle 122 as schematically depicted in FIGS. 1A to 1F. Further, the form of the second compartment 114 is selected in a manner that the second compartment 114 is adapted to be introduced into the container 118 which, thus, comprises both the first compartment 112 and the second compartment 114.

However, the phantom calibration body 110 may also be implemented in a different fashion, specifically by providing the first compartment 112 and the second compartment 114 in manner that both compartments 112, 114 are introduced into a separate container (not depicted here) which may be adapted for receiving both the first compartment 112 and the second compartment 114. In addition, further kinds of embodiments (not depicted here) of the phantom calibration body 110 may also be feasible.

According to the present invention, the first compartment 112 has a first cross-section, wherein the first cross-section of the first compartment 112 exhibits a slight variation of a diameter 124 along a lateral extension or length 126 of the first compartment 112. In contrast hereto, the second compartment 114 has a second cross-section wherein the second cross-section of the second compartment 114 in this exemplary embodiment is generated by a pair of opposing sides 128, 130, which exhibit a non-parallel arrangement a lateral extension or length 132 of the second compartment 114. As schematically depicted in FIGS. 1A to 1F, the pair of the opposing sides 128, 130 is inclined with respect to each other by an angle α of 5° to 45°, specifically of 15° to 30°, as depicted here. As a result, the second compartment 114 in this exemplary embodiment comprises a triangularly varying cross-section, resulting in a linearly increasing or decreasing diameter 134 along the length 132 of the second compartment 114. The particular advantages of this exemplary embodiment of the second compartment 114 are described above and/or below in more detail.

Further according to the present invention, the first compartment 112 of the phantom calibration body 110 is filled with a first solution which comprises a calibration substance having a first concentration. For a purpose of filling the first solution into the first compartment 112, the first compartment 112 can in the exemplary embodiment of FIGS. 1A and 1C to 1F be opened by removing the lid 120. In contrast hereto, the second compartment 114 is filled with a second solution comprising the same calibration substance as filled in the first compartment 112 but having a second concentration, wherein the second concentration differs from the first concentration. For a purpose of filling the second solution into the second compartment 114, the second compartment 114 in the exemplary embodiment of FIGS. 1A to 1F comprises a second opening 136. However, other opportunities for filling the first solution into the first compartment 112 may exist, such as first openings 138 introduced into the lid 120 and specifically adapted for this purpose. However, further opportunities may also exist here.

In the exemplary embodiment as illustrated herein, the calibration substance is polyvinylpyrrolidone (PVP), wherein a different calibration substance as described elsewhere herein may equally be selected. Without restricting the scope of the present invention, the first concentration may, preferably, be selected to provide an ADC of 1.42 $\mu m^2/ms$ at room temperature (21° C.) for the first compartment 112 while the second concentration may, preferably, be selected to provide an ADC of 0.87 $\mu m^2/ms$ for the second compartment 114 in the exemplary embodiment as illustrated herein. As a result, the first concentration used for the first solution comprised by the first compartment 112 has, exemplarily, been selected as 15% (w/w) PVP (K30) while the second concentration as used for the second solution comprised by the second compartment 114 has, exemplarily, been selected as 30% (w/w) PVP (K30), such that, in this particular example, both concentrations differ with respect to each other by a concentration of 15% (w/w). However, other concentrations may also be feasible.

In particular contrast to US 2017/0242090 A1, the first solution and the second solution have a single K-value, such K15, K30 or K90 in the case of PVP, wherein the K-value here refers to a molecular weight of PVP. As a result, the calibration substance does not comprise a dedicated mixture of polymers having a high molecular weight as denoted by a first K-value and a low molecular weight as denoted by a second K-value which considerably differs from the first K-value but only a regular solution having have the selected single K-value. By way of example, an aqueous solution of PVP may be generated by using PVP powder, preferably, as described in DE 737 663 A.

As a result, form, size, and respective arrangement of the two individual compartments 112, 114 within the phantom calibration body 110 are provided in a manner that the two individual compartments 112, 114 of the phantom calibration body 110 are adapted in order to be capable of mimicking two types of the tissues, specifically, the benign tissue and the malignant tissue, of an examined body region, such as a mammal liver. However, further body regions may also be selected.

In a further exemplary embodiment (not depicted here), the phantom calibration body 110 may, additionally, comprise a thermometer unit which may be designed for determining a temperature. Herein, the thermometer unit may be attached to the phantom calibration body 110 or comprised by the phantom calibration body 110, such as within the container 118. However, further arrangements of the thermometer unit may also be feasible.

As further illustrated in FIG. 1F, the lid 120 may be used not only to cover to first compartment 112 but also the container 118, such as in order to provide an additional protection for keeping both the first solution and the second solution within the phantom calibration body 110 over a long time, thus, avoiding, a spilling of the first solution and/or the second solution or a partition thereof from the phantom calibration body 110. For this purpose, the lid 120 may, as depicted in FIG. 1F, be attached to the container 118 by using screws. However, other kinds of closing one or both of the two individual compartments 112, 114 may be feasible. By way of example, the two individual compartments 112, 114 may, after being filled with the calibration substance, be closed without being able to be reopened without a danger of destroying the respective compartment, such as by applying an adhesive or a welding procedure.

FIG. 2 schematically illustrates a computer-implemented method 140 for determining at least one quantitative diffusion parameter extracted for characterization of a tissue being suspicious to a tumorous modification in magnetic resonance imaging (MRI) according to the present invention.

Herein, the method 140 comprises a first step a) of placing 142 a phantom calibration body, in particular the phantom calibration body 110 of FIG. 1, in a vicinity of the tissue. As already indicated above, step a) comprises the placing 142 of the phantom calibration body 110 in a manner that a single image of the tissue under examination and of the phantom calibration body 110 can be obtained. Herein, the phantom calibration body 110 can, in particular, have a design which may allow placing the phantom calibration body 110 within one of the MR coils of the MRI device. For example, the phantom may be placed in an reception of the body matrix coil. Thus, the phantom may, in general, be placed in each MR vendor machine independent of the actual coil design.

Further, the method 140 comprises a further step b) of receiving 144 raw magnetic resonance imaging (MRI) data being recorded by applying at least one diffusion weighted imaging (DWI) sequence concurrently to the tissue and to the phantom calibration body 110. Herein, an apparent diffusion coefficient (ADC) of the tissue may be extracted from the raw MRI data. Alternatively, a diffusional kurtosis coefficient (DKC), Intravoxel incoherent motions' (IVIM), or 'fractional order calculus' (FROC) may also be applied. Further, the exemplary method 140 as depicted here may, additionally, comprise an optional further step of post-processing 146 the raw MRI data as received in step b).

In an exemplary embodiment, a tissue undergoes a magnetic resonance (MR) examination, wherein a first MR device denoted by "MR1" may be employed. Using the first MR device MR1, the ADC of the tissue of a liver lesion may provide an ADC value of 1.9 $\mu m^2/ms$, thus, indicating a benign tissue. Consequently, in the first solution in the phantom calibration body 110 which is subject of being measured concurrently with the tissue an ADC value of 1.9 $\mu m^2/ms$ may, preferably, be adjusted. Later, a further examination may be performed with a second MR device denoted by "MR2" originating from a different vendor. Using the second MR device MR2, the ADC value obtained for a liver lesion may be 1.2 $\mu m^2/ms$, which would, accordingly to the state of the art procedures, indicate a malignant liver. However, the first solution as used in the phantom calibration body 110 which is measured concurrently with the tissue, provides as well an ADC value of 1.2 $\mu m^2/ms$, thus, clarifying that no change of the ADC value of the lesion but only a change of the parameters due to different setting of the second MR device MR2 has been occurred.

Irrespective whether the optional further step of post-processing 146 the raw MRI data has been performed or omitted, a further step c) of extracting 148 at least one quantitative diffusion parameter of the tissue from the raw MRI data is comprised by the method 140, wherein, during the extracting 148, the corresponding quantitative diffusion parameter of the phantom calibration body is taken into account. In particular, by applying Equation (1) above to a volume of interest in the first solution in the phantom calibration body 110, using the known ADC value for the first solution at a given temperature and a the signal $S_0$ which has been acquired for b=0, actually applied b-values by the MR scanner can be estimated, which may, in general, differ from the b-values as entered by the operator into the MR scanner user interface. As a result, the actually applied b-values may, subsequently, be used to determine the desired two-dimensional ("map") or three-dimensional representation of the at least one selected quantitative diffusion parameter of the tissue, specifically the ADC map, in the tissue which has been acquired, concurrently, during the same measurement. In the previous example as provided above, this procedure leads to obtaining the correct value of 1.9 $\mu m^2/ms$ by using the second MR device MR2, too.

Table 1 provides a comparison of three MR examinations performed in a tissue of a particular tissue pursuant to the method according to the present invention and pursuant to known procedures according to the state of the art.

TABLE 1

MR Examination of the same tissue

| MR device | Quantitative ADC data for phantom | Quantitative ADC data for tissue | State-of-the-art result Tissue rating | Result pursuant to invention Tissue rating |
|---|---|---|---|---|
| MR1 | 2.0 $\mu m^2/ms$ | 2.0 $\mu m^2/ms$ | Baseline (e.g. benign) | Baseline (e.g. benign) |
| MR2 | 1.0 $\mu m^2/ms$ | 1.0 $\mu m^2/ms$ | Significant change to data recorded with MR1 | No change after correction using phantom |
| MR3 | 2.0 $\mu m^2/ms$ | 1.0 $\mu m^2/ms$ | No change to previous data recorded with MR2 | Significant change after correction using phantom |

As a result, in a first MR examination in a first MR device MR1 the tissue reveals a lesion with an ADC of 2.0 $\mu m^2/ms$, which is considered as benign in the tissue rating.

In a second MR examination in a second MR device MR2, the tissue now shows a significant change in the lesion ADC value to 1.0 $\mu m^2/ms$. This observation could trigger a change in therapy of the corresponding patient without the present invention. However, when applying the method according to the present invention, it becomes apparent that not only the ADC of the lesion but also the ADC of the phantom has changed, thus, the observed change can be attributed to the different MR device rather than to the lesion itself. Using the above-mentioned correction scheme for the b-values, after correction, one would then obtain the correct value 2.0 $\mu m^2/ms$ in MR2, too.

In a third MR examination in a third MR device MR3, no change seems to be present in the lesion due to an observed ADC value of 1.0 $\mu m^2/ms$. However, when applying the method according to the present invention, it becomes apparent that the ADC did actually change since the phantom clearly demonstrates that, in comparison to the previous examination using the second MR device MR2, there is occurs a mismatch between ADC in the phantom and the tissue.

As a result, the method according to the present invention allows determining absolute quantitative parameters in an individualized fashion for each individual origin of the tissue, specifically for each patient, independent from various times of recording, applied software algorithms for post-processing of the raw MRI data, MR devices, MR vendors, etc. In contrast to the current state of the art, the present invention, thus, allows using the absolute quantitative data extracted from the phantom measured with every tissue for comparability of quantitative data, which appears as a prerequisite for introducing quantitative DWI imaging into clinical routine.

LIST OF REFERENCE NUMBERS 110 phantom calibration body
112 first compartment
114 second compartment
116 first receptacle
118 container
120 lid
122 second receptacle
124 diameter
126 length
128 opposing side
130 opposing side
132 length 134 diameter
136 second opening
138 first opening
140 method
142 placing of the phantom calibration body
144 receiving raw magnetic resonance imaging (MRI) data
146 post-processing the raw MRI data
148 extracting quantitative diffusion parameter of the tissue from the raw MRI data.

LIST OF CITED REFERENCES

[1] Freitag M T, Bickelhaupt S, Ziener C, Meier-Hein K, Radtke J P, Mosebach J, et al. Selected clinically established and scientific techniques of diffusion-weighted MRI: In the context of imaging in oncology. Der Radiologe 2016; 56(2):137-47.
[2] Radbruch A, Weberling L D, Kieslich P J, Eidel O, Burth S, Kickingereder P, et al. Gadolinium retention in the dentate nucleus and globus pallidus is dependent on the class of contrast agent. Radiology. 2015; 275(3):783-91.
[3] Errante Y, Cirimele V, Mallio C A, Di Lazzaro V, Zobel B B, Quattrocchi C C. Progressive increase of T1 signal intensity of the dentate nucleus on unenhanced magnetic resonance images is associated with cumulative doses of intravenously administered gadodiamide in patients with normal renal function, suggesting dechelation. Invest Radiol. 2014; 49(10):685-90.
[4] Kanda T, Ishii K, Kawaguchi H, Kitajima K, Takenaka D. High signal intensity in the dentate nucleus and globus pallidus on unenhanced T1-weighted MR images: relationship with increasing cumulative dose of a gadolinium-based contrast material. Radiology. 2014; 270(3):834-41.
[5] McDonald R J, McDonald J S, Kallmes D F, Jentoft M E, Murray D L, Thielen K R, et al. Intracranial Gadolinium Deposition after Contrast-enhanced MR Imaging. Radiology. 2015; 275(3):772-82.
[6] Othman E, Wang J, Sprague B L, Rounds T, Ji Y, Herschorn S D, et al. Comparison of false positive rates for screening breast magnetic resonance imaging (MRI) in high risk women performed on stacked versus alternating schedules. SpringerPlus. 2015; 4:77.
[7] Baltzer P A T, Benndorf M, Dietzel M, Gajda M, Runnebaum I B, Kaiser W A. False-Positive Findings at Contrast-Enhanced Breast MRI: A BI-RADS Descriptor Study. American Journal of Roentgenology. 2010; 194(6):1658-63.
[8] Quon J S, Moosavi B, Khanna M, Flood T A, Lim C S, Schieda N. False positive and false negative diagnoses of prostate cancer at multi-parametric prostate MRI in active surveillance. Insights into Imaging. 2015; 6(4):449-63.
[9] Bammer R. Basic principles of diffusion-weighted imaging. Eur J Radiol. 2003; 45(3): 169-84.
[10] Koh D M, Collind D J, Orton M R. Intravoxel incoherent motion in body diffusion-weighted MRI: reality and challenges. AJR Am J Roentgenol. 2011; 196(6):1351-61.
[11] Yablonskiy D A, Bretthorst G L, Ackerman J J. Statistical model for diffusion attenuated MR signal. Magnetic resonance in medicine. 2003; 50(4):664-9.
[12] Jensen J H, Helpern J A, Ramani A, Lu H, Kaczynski K. Diffusional kurtosis imaging: the quantification of non-gaussian water diffusion by means of magnetic resonance imaging. Magnetic resonance in medicine. 2005; 53(6):1432-40.
[13] Iima M, Yano K, Kataoka M, Umehana M, Murata K, Kanao S, et al. Quantitative non-Gaussian diffusion and intravoxel incoherent motion magnetic resonance imaging: differentiation of malignant and benign breast lesions. Invest Radiol. 2015; 50(4):205-11.
[14] Sui Y, Wang H, Liu G, Damen F W, Wanamaker C, Li Y, et al. Differentiation of Low- and High-Grade Pediatric Brain Tumors with High b-Value Diffusion-weighted MR Imaging and a Fractional Order Calculus Model. Radiology. 2015; 277(2):489-96.
[15] Panagiotaki E, Walker-Samuel S, Siow B, Johnson S P, Rajkumar V, Pedley R B, Lythgoe M F, and Alexander D C; Noninvasive Quantification of Solid Tumor Microstructure Using VERDICT MRI; Cancer Res; 74(7) Apr. 1, 2014, 1902-12.
[16] Barbieri, S., Bronnimann, M., Boxler, S. et al. Differentiation of prostate cancer lesions with high and with low Gleason score by diffusion-weighted MRI. Eur Radiol 2016, pp 1-9.
[17] Sui, Y., H. Wang, et al. (2015). "Differentiation of Low- and High-Grade Pediatric Brain Tumors with High b-Value Diffusion-weighted MR Imaging and a Fractional Order Calculus Model." Radiology 277(2): 489-496.
[18] Wagner F., Laun F. B., Kuder T. A., Bickelhaupt S. et al., Temperature and concentration calibration of aqueous polyvinylpyrrolidone (PVP) solutions for isotropic diffusion MRI phantoms, Benjamini D., ed. PLoS ONE 2017; 12 (6): e0179276; doi.•10.1371/journal.pone.0179276.
[19] Kathryn E. Keenan et al: "Design of a breast phantom for quantitative MRI", J. Magn. Res. Imaging, Vol. 44, No. 3, 2016, 610-619.
[20] Laun F B, Fritzsche K H, Kuder T A, Stieltjes B. Einfuhrung in die Grundlagen und Techniken der Diffusionsbildgebung. Radiologe 2011; 51(3):170-179.

The invention claimed is:
1. A phantom calibration body for a method for determining at least one quantitative diffusion parameter extracted for characterization of a tissue being suspicious to a tumorous modification in magnetic resonance imaging, wherein the phantom calibration body is designed for being characterized during characterization of the tissue by the magnetic resonance imaging, the phantom calibration body comprising
 a first compartment having a first cross-section, the first compartment being filled with a first solution comprising a calibration substance having a first concentration;
 a second compartment having a second cross-section, the second cross-section having at least two different partitions with differing diameters, wherein the second compartment is filled with a second solution comprising the calibration substance having a second concentration, the second concentration differing from the first concentration, wherein the second cross-section of the second compartment exhibits a pair of opposing sides having a non-parallel arrangement, the opposing sides being inclined by an angle of 5° to 45° with respect to each other;
  wherein the first compartment comprises a firs receptacle, wherein the second compartment comprises a second receptacle, wherein the first receptacle and the second receptacle are comprised by a container; and
  wherein the first receptacle is the container and wherein in the second receptacle is comprised by the first compartment.
2. The phantom calibration body of claim 1, further comprising at least one first opening designed for filling the first solution into the first compartment and at least one second opening being different from the first opening, wherein the second opening is designed for filling the second solution into the second compartment.

3. The phantom calibration body of claim 1, wherein the calibration substance comprises a substance is selected from at least one of polyvinylpyrrolidone, a polyvinyl alcohol, a polyacrylamide, a polyacrylate, a polyethylene glycol, a polysaccharide, cellulose, a derivative thereof, or a copolymer thereof.

4. The phantom calibration body of claim 3, wherein the first concentration and the second concentration are selected from a concentration of 0.01% (w/w) to 100% (w/w).

5. The phantom calibration body of claim 4, wherein the second concentration differs from the first concentration by at least 0.1% (w/w).

6. The phantom calibration body of claim 1, wherein the first concentration and the second concentration are selected from two individual concentrations which are adapted for mimicking two different types of the tissue.

7. The phantom calibration body of claim 1, wherein the first solution and the second solution have a single K-value.

8. The phantom calibration body of claim 1, further comprising a thermometer unit designed for determining a temperature, the thermometer unit being attached to the phantom calibration body or comprised by the phantom calibration body.

9. The phantom calibration body of claim 1, wherein the second cross-section of the second compartment exhibits a pair of opposing sides having a non-parallel arrangement, the pair of the opposing sides being inclined by an angle of 15° to 30° with respect to each other.

10. The phantom calibration body of claim 4, wherein the second concentration differs from the first concentration by at least 1% (w/w).

11. The phantom calibration body of claim 4, wherein the first concentration is selected of 5% to 60%.

12. The phantom calibration body of claim 4, wherein the second concentration is selected of 20% to 75%.

13. A computer-implemented method for determining at least one quantitative diffusion parameter extracted for characterization of a tissue being suspicious to a tumorous modification in magnetic resonance imaging, wherein the method comprises the steps of:
   a) placing a phantom calibration body of claim 1 in a vicinity of the tissue;
   b) receiving raw magnetic resonance imaging (MRI) data being recorded by applying at least one diffusion weighted imaging (DWI) sequence concurrently to the tissue and to the phantom calibration body;
   c) extracting at least one quantitative diffusion parameter of the tissue from the raw MRI data, wherein the corresponding quantitative diffusion parameter of the phantom calibration body is considered.

14. The method of claim 13, wherein the quantitative diffusion parameter of each the tissue and the of the phantom calibration body is extracted from the raw MRI data by using at least one quantification scheme, the quantification scheme being selected from 'diffusional kurtosis imaging' (DKI), 'apparent diffusion coefficient' (ADC), 'intravoxel incoherent motions' (IVIM), or 'fractional order calculus' (FROC).

15. The method of claim 13, wherein a minimum lesion size capable of differentiating between two types of the tissue is obtained by determining the corresponding quantitative diffusion parameter for at least two different partitions of the second compartment of the phantom calibration body.

16. The method of claim 13, wherein the phantom calibration body is placed such that a single image of the tissue under examination and of the phantom calibration body is obtained.

* * * * *